United States Patent [19]

Bakker et al.

[11] Patent Number: 5,508,036
[45] Date of Patent: Apr. 16, 1996

[54] DEVICES FOR PREVENTING TISSUE ADHESION

[75] Inventors: Dirkjan Bakker, Alphen a/d Rijn; Erica A. Bakkum, AL Haarlem; Clemens A. van Blitterswijk, Hekendorp, all of Netherlands

[73] Assignee: Osteotech, Inc., Eatontown, N.J.

[21] Appl. No.: 78,350

[22] Filed: Jun. 21, 1993

Related U.S. Application Data

[63] Continuation-in-part of Ser. No. 873,441, Apr. 24, 1992, abandoned.

[51] Int. Cl.⁶ ........................................... B32B 3/26
[52] U.S. Cl. .................... 424/424; 424/426; 428/314.4; 428/315.5; 428/318.6; 428/319.7; 428/318.8; 604/358; 604/369; 604/370; 604/371; 606/1; 128/899; 521/51; 521/61; 521/916
[58] Field of Search ....................... 424/426, 424; 428/314.4, 315.5, 318.6, 319.7, 318.8; 604/358, 369, 370, 371; 606/1; 128/899; 521/51, 61, 916

[56] References Cited

U.S. PATENT DOCUMENTS

| | | | |
|---|---|---|---|
| 4,704,130 | 11/1987 | Gilding et al. | 623/66 |
| 4,740,282 | 4/1988 | Gesser et al. | 204/165 |
| 5,002,571 | 3/1991 | O'Donnell et al. | 623/6 |
| 5,185,408 | 2/1993 | Tang et al. | 525/415 |

OTHER PUBLICATIONS

Lawson, et al., *SPINE*, vol. 16, No. 6 Supplement, pp. S222–S226 (1991) Jun.
A. M. Reed and D. K. Gilding; Biodegradable polymers for use in Surgery; Polymer; 1981; Apr.; vol. 22; pp. 499–504.
D. K. Gilding and A. M. Reed; Biodegradable Polymers for Use in Surgery; Polymer; Dec., 1979; vol. 20; pp. 1454–1458.

*Primary Examiner*—James J. Seidleck
*Assistant Examiner*—R. F. Johnson
*Attorney, Agent, or Firm*—Elliot M. Olstein; Raymond J. Lillie

[57] ABSTRACT

A device for preventing adhesions or binding of tissue to tissue or of tissue to bone which comprises a composite of a first layer and a second layer, each of which comprises a biodegradable polymer. The first layer is selected from the group consisting of a non-porous layer and a porous layer having a pore size no greater than 3μ. The second layer has pores which have a pore size of from about 30μ to about 250μ. Such a composite device provides for tissue growth into the second layer, while the first layer acts as an adhesion-preventing barrier, and enables attachment of the device to tissue without suturing. Alternatively, the device comprises the first layer hereinabove mentioned and a second layer which is an adherence layer and which adheres to tissue and/or bone.

22 Claims, No Drawings

DEVICES FOR PREVENTING TISSUE ADHESION

This application is a continuation-in-part of application Ser. No. 873,441, filed Apr. 24, 1992, now abandoned.

This invention relates to devices, such as films, sheets, or blocks for preventing the adhesion of tissue to tissue or of tissue to bone. More particularly, this invention relates to devices, formed from polymeric materials, for preventing tissue adhesion.

In the field of internal medical care, such as internal surgery, there is a need for tissue regeneration devices which may prevent complications such as adhesions in the post-operative healing period. Adhesions which may be formed include the adhesion of tissue to tissue or of tissue to bone. As generally known, the occurrence of post-operative adhesion formation after internal surgery is a major problem in abdominal surgery. For instance, in gynecological patients adhesion may affect fertility. As in about 70% of the gynecological abdominal surgical interventions adhesions do occur, it is evident that there is a need for a suitable method for preventing the above-identified adhesions, and the complications and patient discomfort associated therewith.

It has been known to separate adjacent internal bodily surfaces by interposing a mesh or film so that during tissue regeneration following surgery no contact exists between the surfaces.

One material which has been employed to prevent adhesions is an expanded polytetrafluoroethylene material known as Gore-Tex®. This material, however, is not hemostatic and is non-degradable by the human body. Thus the implant remains in the body, and, if necessary, must be removed surgically following the healing process.

Another material is a mesh barrier of carboxymethylcellulose known as Interceed®. This material, however, may not be applied in a blood-rich environment as under such circumstances the material quickly loses its barrier function.

Gilding and Reed, in *Polymer*, Vol. 20 pgs. 1454–1458 (December 1979) and in *Polymer*, Vol. 22, pgs. 499–504 (April 1981), disclose films formed from poly(ethyleneoxide) and polyethylene terephthalate, as barrier materials to prevent surgical adhesions.

It is an object of the present invention to provide a device for preventing the binding of tissue to tissue or of tissue to bone wherein the device prevents such binding while being sufficiently pliable as well as providing for growth of tissue, such as fibrous tissue, into the device.

In accordance with an aspect of the present invention, there is provided a device for preventing the binding of tissue to tissue or of tissue to bone. The term "tissue" as used herein means tissue other than bone (e.g., fibrous tissue, soft tissue, muscle tissue, etc.) The device comprises a composite of a first layer and a second layer. The first and second layer each are comprised of a biodegradable or bioerodable polymer. The polymers which make up the first and second layers may be the same or different. The first layer is a "dense" layer which acts as a barrier layer and which is non-porous (i.e., the layer essentially has no pores) or if porous, essentially all of the pores have a pore size no greater than 3µ. Preferably, the first layer is non-porous. Also, the first layer preferably has a high water content. The first layer, in general, also prevents the ingrowth of tissue. In general, the first layer has a thickness of from about 5µ to about 80µ, preferably from about 15µ to about 50µ.

The second layer, which also comprises the polymer hereinabove described, is a "porous" layer which includes pores having a pore size of at least about 30µ. In most cases the pore size does not exceed about 250µ. In general, the pores of the second layer permit the ingrowth of tissue. Preferably, the pore size is from about 75µ to about 215µ.

In general, the second layer has a thickness of from about 30µ to about 250µ, and a porosity of from about 30% to about 80%, preferably from about 35% to about 70%. The term "porosity," as used herein, means the volume of pores per unit volume multiplied by a factor of 100. Porosity may be determined by optical microscopy according to the procedure described in ASTM Designation E562-83, entitled "Standard Practice for Determining Volume Fraction by Systematic Manual Point Count."

In another alternative, the device may be used as a block to prevent the binding of tissue to tissue or tissue to bone. Such barriers or blocks may have a thickness of from about 200µ to about 10 mm, and may be employed as guided tissue regeneration devices or as spinal barriers.

Although the scope of the present invention is not to be limited to any theoretical reasoning, it is believed that the first, or dense, layer acts as a barrier layer, i.e., the first layer prevents adhesion of tissue to tissue or of tissue to bone. The first, or dense, layer, also prevents the ingrowth of tissue into the first, or dense, layer. The first layer also invites little fibrosis because there is little protein absorption which is involved in cell attachment and, hence, little fibrosis. The second, or porous, layer allows the growth of tissue, such as vascularized fibrous tissue, into the pores, which enables the device to become anchored to the tissue without requiring suturing of the device to the tissue. The second, or porous, layer also allows immediate anchorage of the device to the tissue because of capillary activity (i.e., the device adheres to wet surfaces), and allows intermediate anchorage because of the attachment of fibrin strands and the like onto and into the porous layer. Vascularized fibrous tissue ingrowth ensures a permanent anchorage until the material of the device is resorbed. Applicants have also found that the device forms a "scaffolding," which enables mesothelial tissue to grow over the device when the device is placed over a damaged piece of tissue. As the mesothelium grows over the device, the mesothelium acts as a natural barrier against tissue adhesion.

The first layer, which essentially has no pores, or if porous, essentially all of the pores have a pore size no greater than 3µ, may include some pores which interconnect and/or may have some pores having a pore size greater than 3µ as long as the presence of such pores does not permit the growth of tissue into the first layer.

The second layer, which, in general, includes pores having a pore size of at least about 30µ, and which in general do not exceed about 250µ, may also include pores having a pore size less than about 30µ or greater than about 250µ, provided that the second layer provides for the growth of tissue into the second layer as hereinabove described.

The polymer is one which is biodegradable, or bioerodable, i.e., the polymer is broken down gradually by the body after implantation. After a period of time, which may vary depending upon various factors such as the thickness of the device, the proportion of the components of the polymer, and the specific use of the polymer, the polymer loses its unitary structure. For example, the polymeric device breaks into pieces, and may eventually be completely resorbed. Preferably, the polymer is bioabsorbable in addition to being biodegradable; i.e., the polymer is resorbed by the body such that the polymeric device becomes essentially non-detectable at the site of implantation. As hereinabove stated, the polymeric device forms a "scaffolding" which enables mesothelial tissue to grow over the device when the device is placed over a damaged piece of tissue, whereby the mesothelium grows over the device and acts as a natural barrier against tissue adhesion. After the mesothelium has grown over the device, the polymeric structure of the device begins to break down such that the device loses its unitary structure, and the device no longer functions as a barrier. The term "biodegradable" as used herein encompasses the complete resorption of the polymeric materials of the device by the body as well as a breakdown of the polymeric structure of the device without complete resorption of the device; i.e., the structure of the device is broken down into a plurality of pieces which are not completely resorbed.

Polymers which may be employed to form the first and second layers of the composite device include, but are not limited to, polyethers (both substituted and unsubstituted); poly (hydroxyethyl methacrylate); polyurethanes; polyamides; polyanhydrides; polysulfones; polycaprolactones; polyglycolides; polylactides, such as, for example, polylactic acid; polyphosphazenes; poly amino acids; poly-orthoesters; polyiminocarbonates; polytrimethylene carbonates; polyhydroxymethacrylates; polyhydroxybutyrate; polyglyconate; polydioxanone; polyhydroxyvalerate; polyhydroxybutyrate/polyhydroxyvalerate copolymers; polyester urethanes; polyether urethanes, and polyurethane urea. In one embodiment, the polymer may be a copolymer formed from any combination of the above components. The polymer may also be a copolymer of a first, or "soft" component selected from the group consisting of polyethers (both substituted and unsubstituted) and poly (hydroxyethyl methacrylate); and a second, or "hard" component selected from the group consisting of urethanes, amides, and esters.

It is also contemplated that within the scope of the present invention that the first layer may be formed from one polymer, and the second layer may be formed from another polymer. For example, the first layer may be formed from a polyether/polyester copolymer, such as a polyethylene glycol/polybutylene terephthalate copolymer, and the second layer may be formed from polylactic acid or a polyglycolide.

In one embodiment, the polymer is in the form of a hydrogel. A hydrogel, because of its hydrophilicity, invites little fibrosis, because there is little protein absorption which is involved in cell attachment and, hence, little fibrosis. The hydrophilicity of the dense layer prevents fibrous tissue adhesion, while the hydrophilicity of the porous layer aids the growth of tissue into the pores, whereby immediate anchorage of the device to the tissue is achieved.

In one embodiment, the first and second layers are formed from a polymer which is a copolymer comprised of a first, or soft component, and a second, or hard component, as hereinabove described.

The first, or soft, component, which is preferably hydrophilic, imparts pliability or elasticity to the polymer, and enables the polymer to be biodegradable, while the second, or hard, component imparts structural stability to the polymer. One therefore may increase or decrease the pliability or elasticity, as well as the hydrophilicity of the polymer by varying the amounts of the soft and hard components in the polymer.

The soft component may be present in an amount of from about 30 wt. % to about 80 wt. % of the copolymer, preferably from about 50 wt. % to about 80 wt. %. In general, the copolymer becomes more elastomeric as the amount of the soft component increases. In a preferred embodiment, the soft component is in the form of a hydrogel.

In one embodiment, the soft component is a polyether, preferably a polyalkylene glycol. The polyalkylene glycol may be selected from the group consisting of polyethylene glycol, polypropylene glycol, and polybutylene glycol. In one embodiment, the polyalkylene glycol is polyethylene glycol.

The hard component may be present in the copolymer in an amount of from about 20 wt. % to about 70 wt. %, preferably from about 20 wt. % to about 50 wt. %. The hard component stabilizes the soft component in water, as well as provide the physical characteristics of the polymer, and provides mechanical strength to the copolymer.

The hard component may be selected from the group consisting of urethanes, amides, and esters. The ester may have the following structural formula:

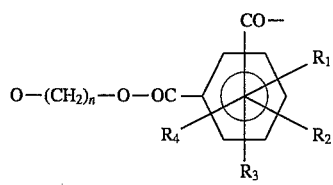

, wherein n is from 2 to 8, and each of $R_1$, $R_2$, $R_3$, and $R_4$ is hydrogen, chlorine, nitro-, or alkoxy, and each of $R_1$, $R_2$, $R_3$, and $R_4$ is the same or different. Alternatively, the ester is derived from a binuclear aromatic diacid having the following structural formula:

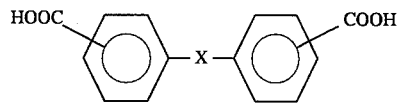

, wherein X is —O—, —$SO_2$—, or —$CH_2$—.

Preferably, the hard component is an ester having the following structural formula:

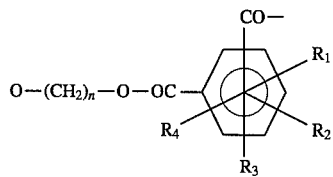

, wherein n is from 2 to 8, and each of $R_1$, $R_2$, $R_3$, and $R_4$ is hydrogen, chlorine, nitro-, or alkoxy, and each of $R_1$, $R_2$, $R_3$, and $R_4$ is the same or different. More preferably, each of $R_1$, $R_2$, $R_3$, and $R_4$ is hydrogen.

In a preferred embodiment, the copolymer is a segmented thermoplastic biodegradable polymer comprising a plurality of recurring units of the first component and units of the second component. The first component comprises from about 30 wt. % to about 80 wt. %, based upon the weight of the copolymer, of units of the formula:

—OLO—CO—R—CO—, wherein L is selected from the group consisting of a divalent radical remaining after removal of terminal hydroxyl groups from a poly (oxyalkylene) glycol; and a polymer including a first moiety and a second moiety, said first moiety being a polyalkylene glycol and said second moiety being selected from the group consisting of glycine anhydride; alloxan; uracil; 5,6-dihydrouracil; glycolic acid; lactic acid; and lactones, such as, for example, dicarboxiylic acid lactones. The second component is present in an amount of from about 20 wt. % to about 70 wt. %, based on the weight of the copolymer, and is comprised of units of the formula:

—OEO—CO—R—CO—. E is an organic radical selected from the group consisting of a substituted or unsubstituted alkylene radical having from 2 to 8 carbon atoms, and a substituted or unsubstituted ether moeity. R is a substituted or unsubstituted divalent radical remaining after removal of carboxyl groups from a dicarboxylic acid.

The poly (oxyalkylene) glycol, in one embodiment, may be selected from the group consisting of poly (oxyethylene) glycol, poly (oxypropylene) glycol, and poly (oxybutylene) glycol. Preferably, the poly (oxyalkylene) glycol is poly (oxyethylene) glycol.

The poly (oxyethylene) glycol may have a molecular weight of from about 200 to about 4,000, preferably from about 300 to about 2,000, more preferably from about 600 to about 1,500.

In one embodiment, E is a radical selected from the group consisting of a substituted or unsubstituted alkylene radical having from 2 to 8 carbon atoms, preferably having from 2 to 4 carbon atoms. Preferably, the second component is selected from the group consisting of polyethylene terephthalate, polypropylene terephthalate, and polybutylene terephthalate. In one embodiment, the second component is polybutylene terephthalate.

In a most preferred embodiment, the copolymer is a polyethylene glycol/polybutylene terephthalate copolymer.

In one embodiment, the polyethylene glycol/polybutylene terephthalate copolymer may be synthesized from a mixture of dimethylterephthalate, butanediol (in excess), polyethylene glycol, an antioxidant, and a catalyst. The mixture is placed in a reaction vessel and heated to about 180° C., and methanol is distilled as transesterification occurs. During the transesterification, the ester bond with methyl is replaced with an ester bond with butyl. In this step the polyethylene glycol does not react. After transesterification, the temperature is slowly raised to about 245° C. and a vacuum (finally less than 0.1 mbar) is achieved. The excess butanediol is distilled and a prepolymer of butanediol terephthalate condenses with the polyethylene glycol to form a polyethylene glycol/polybutylene terephthalate copolymer. A terephthalate moiety connects the polyethylene glycol units to the polybutylene terephthalate units of the copolymer, and thus such copolymer is also sometimes hereinafter referred to as a polyethylene glycol terephthalate/polybutylene terephthalate copolymer, or PEGT/PBT copolymer. In another alternative, polyalkylene glycol/polyester copolymers may be prepared as described in U.S. Pat. No. 3,908,201.

It is to be understood, however, that the scope of the present invention is not to be limited to the specific copolymer hereinabove described, or to any particular means of synthesis.

The polyalkylene glycol/polyester copolymers may, in some instances, be blended with a polyalkylene glycol (such as polyethylene glycol), in an amount of up to 50 wt. % to provide increased elasticity or pliability to the device, if desired. In one embodiment, the alkylene glycol units are linked by terpthalates; however, the terephthalates do not form a segmented copolymer with the alkylene glycol.

The polymers of the present invention are formed into the first and second layers to provide a device such as a film that prevents binding of tissue to tissue or of tissue to bone. In one embodiment, the layer(s) forming the film may be formed by means of an extrusion process. In an extrusion process, a polymeric melt is extruded from an extrusion machine and formed into a film. If the porous layer is prepared by an extrusion process, salt particles, having diameters from about 30μ to about 250μ may be mixed with the polymeric melt to form pores having diameters from about 30μ to about 250μ. Alternatively, the polymer may be blended in the melt with a second polymer, such as, but not limited to, polyvinyl pyrrolidone, polyethylene glycol, or polycaprolactone, in order to form pores in the polymer. After blending, the second polymer forms a co-continuity with the first polymer. The second polymer then is washed out with a non-solvent for the first polymer. When preparing the dense layer, the salt particles, or the second polymer, are not included in the polymeric melt.

Alternatively, the polymer may be liquefied in chloroform at a weight ratio of polymer to chloroform of 1 to 10, and then fibers of the polymer are spun. The fibers are then woven on a rotation axis to produce woven tubings which are cut lengthwise to produce films.

In another embodiment, for producing the second, or porous, layer, a salt-casting technique may be employed. In this procedure, a polymer is liquefied in chloroform at a weight ratio of polymer to chloroform of 1 to 10. A certain amount of salt particles of desired sizes is then added to the polymer solution. Salt particles having diameters from about 30μ to about 250μ resulted in pores with diameters from about 30μ to about 250μ. The salt/polymer solution is then either cast on a glass plate using a film-casting apparatus fixed at the desired height, or used as a dip solution to obtain porous coatings. The ratio of salt to polymer provides a desired porosity. For example, 6 g of salt (eg., sodium citrate or sodium chloride) per gram of polymer results in films with porosities of about 50%.

In another embodiment, the dense layer may be prepared by liquefying a polymer in chloroform at a weight ratio of copolymer to chloroform of 1 to 10. No salt particles are added to the polymer solution. The solution is then cast on a glass plate using a film-casting apparatus fixed at the desired height, or used as a dip solution to obtain a coating.

In one embodiment, after casting, and when a polyalkylene glycol/polyester copolymer is employed, the dense film is immersed in a bath containing a mixture of acetone (about 85 wt. %) and distilled water (about 15 wt. %). Acetone (and acetone/water) is a non-solvent for polyalkylene glycol/polyester copolymers. The copolymers, forming one phase, which are dissolved in chloroform or n-hexane, or ethanol, or methanol (the second phase), coagulate because the chloroform, or n-hexane, or ethanol, or methanol mixes with acetone (the third phase), thereby leaving the copolymer phase alone. The copolymer thus is contained in a solvent/non-solvent system in which they are insoluble. The copolymers not only coagulate but also form a consistent film through phase separation. The above technique may also be employed with copolymer/chloroform/salt mixtures to form porous films having the desired porosity and more round pores.

The dense and porous layers of the device also may be formed by injection molding or melt extrusion techniques. When preparing the porous layer, one may admix salt particles having sizes such as those hereinabove described, or one of the "second polymers" hereinabove mentioned, with the polymer prior to or upon feeding the polymer into the injection molding or melt extrusion device. When preparing the dense layer, one does not add such particles to the polymer.

In another alternative, porous materials may be formed through the use of foaming agents or blowing agents. A foaming agent or blowing agent is an agent that leads to the formation of pores in the polymer through the release of a gas at an appropriate time during processing. Examples of such foaming agents or blowing agents include, but are not limited to, nitrogen, carbon dioxide, chlorofluorocarbons, inorganic carbonate or bicarbonate salts, toluene sulfonyl hydrazide, oxybis (benzene sulfonyl hydrazide), toluene sulfonyl semicarbazide, and azodicarbonamide. In general, such agents are added prior to feeding the polymer to an injection molder or melt extrusion device. The amount of blowing agent added is dependent upon the pore size and the percent porosity desired in the porous layer.

In another alternative, the porous layer may be formed by forming initially a dense polymer layer, which is then subjected to laser treatment, whereby the laser penetrates the polymer and forms pores of a desired pore size.

In yet another alternative, a dense polymer layer may be mixed with a solvent, and the polymer is then melted under pressure. As the pressure is gradually removed, the polymer swells. During the swelling, pores are formed in the polymer.

Alternatives to the above-mentioned polyethylene glycol terephthalate/polybutylene terephthalate copolymer may be prepared if one wishes to enhance the overall hydrophilic (or "soft") or hydrophobic (or "hard") properties of the polymer.

For example, if one wishes to enhance the hydrophobic properties of the polymer, a number of alternatives may be employed. Thus, in one embodiment, E is an ether, and preferably an ether having from 2 to 6 carbon atoms, more preferably from 2 to 3 carbon atoms. In another embodiment, the second component may include a mixture of ether moieties having 2 carbon atoms and 3 carbon atoms.

In one embodiment, diethylene glycol may replace butanediol in the mixture from which the polymer is synthesized. The extra oxygen in diethylene glycol renders the hydrophobic, or "hard", component more hydrophilic, and may render the resulting polymer more flexible; i.e., less hard.

In other embodiments, alternatives to dimethylterephthalate (DMT) may be employed in the mixture from which the polymer is synthesized. In one embodiment, dimethyl-2,5-dihydroxy-terephthalate is employed instead of dimethylterephthalate. The presence of the two hydroxy groups renders the resulting "hard" component more hydrophilic. The greater hydrophilicity may favor hydrolysis in the "soft" component, as well as increase the probability of hydrolysis in the "hard" component. The two hydroxy groups provide increased water solubility, which results in a more rapid degradation. Also, the two hydroxy groups may provide possibilities for metabolic derivatization, which may result in lower toxicity. In addition, dimethyl-2,5-dihydroxy-terephthalic acid, which is liberated after degradation, may induce the calcification process.

In another embodiment, dimethylterephthalate-2,5-diglycinate ester or dimethoxyterephthalate-2,5-diglycinate ester may be employed in place of dimethylterephthalate. Such a diglycinate ester may result in a more hydrophilic structure for the "hard" component.

In yet another embodiment, amino dimethylterephthalate may be employed in the synthesis mixture. The use of amino dimethylterephthalate may provide increased hydrophilicity to the hard component. Also, the presence of the amino group may accelerate degradation.

In a further embodiment, the synthesis mixture may include diethylene glycol in place of butanediol, and one of the above-mentioned dimethylterephthalate derivatives in place of dimethylterephthalate.

In yet another embodiment, a polyethylene glycol "prepolymer" may be employed in the synthesis mixture instead of polyethylene glycol. Prepolymers of polyethylene glycol which may be employed include, but are not limited to, prepolymers of polyethylene glycol with glycine anhydride (2,5-piperazine dione), alloxan, uracil, 5,6-dihydrouracil, glycolic acid, and lactone groups having ester bonds, such as D-,L-isocitric acid lactone.

When D-,L-isocitric acid lactone is employed in the prepolymer, D-,L-isocitric acid is ultimately released upon degradation of the polymer. The released D-,L-isocitric acid may catalyze the hydrolysis of ester bonds, and may also enhance the calcification process by complexing with calcium.

In yet another embodiment, the synthesis mixture may include diethylene glycol, a dimethylterephthalate derivative, and a polyethylene glycol prepolymer. In a preferred embodiment, the polymer is synthesized from a mixture of diethylene glycol, dimethoxyterephthalate-2,5-diglycinate ester, and a prepolymer of polyethylene glycol and D-,L-isocitric acid lactone ester. Such a polymer has the following structure:

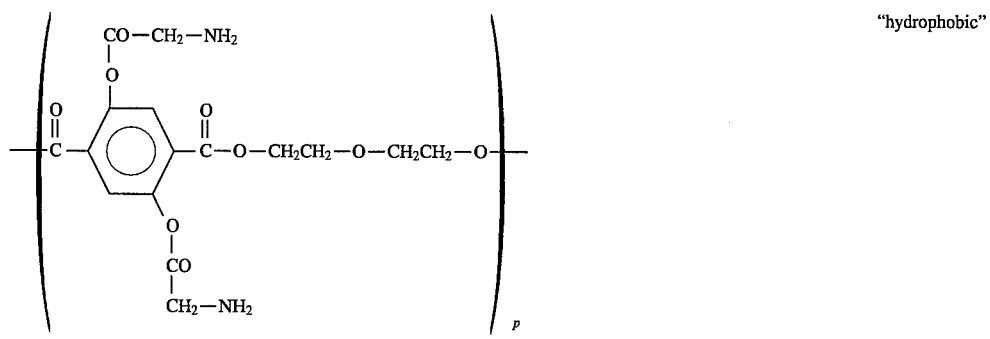

"hydrophobic"

-continued

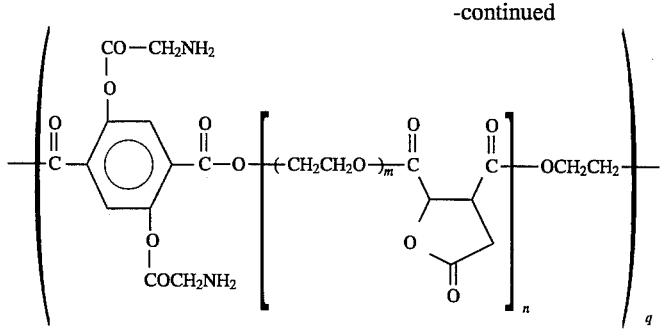

m is from about 10 to about 100; n is from 1 to about 10; p is from 1 to about 30; and q is from 1 to about 30.

In another embodiment, the polymer may include a polyphosphazene, to which the hydrophilic ("soft") and hydrophobic ("hard") components may be attached.

In general, polyphosphazenes have the following structural formula.

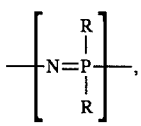

wherein R is an alkoxy, aryloxy, amino, alkyl, aryl, heterocyclic unit (e.g., imidazolyl), or an inorganic or organometallic unit.

In general, polyphosphazene derivatives may be synthesized from a precursor polymer known as poly (dichlorophosphazene) by macromolecular substitution of the chloride side moieties. The broad choice of side group structures which may be attached to the phosphorus atoms enables one to attach any of a variety of hydrophilic ("soft") and hydrophobic ("hard") components to the polyhosphazene. In addition, degradation inducers and other inert substituents may be attached to the polyhosphazene polymer backbone as well.

Thus, in accordance with another embodiment, the polymer has the following structural formula:

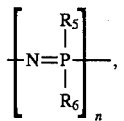

wherein n is from about 50 to about 2,000, and each of $R_5$ and $R_6$ is selected from the group consisting of a first, or soft component which preferably is hydrophilic and imparts pliability or elasticity to the polymer; a second hydrophobic, or hard component which imparts structural stability to the polymer; a third component which induces degradation of the polyer; and a fourth inert component. From at least about 10% of the total $R_5$ and $R_6$ moieties must be substituted with the first component.

Preferably, from about 10% to about 90% of the total $R_5$ and $R_6$ moieties are the first component, and from about 10% to about 70% of the total $R_5$ and $R_6$ moieties are the second component.

More preferably, from about 50% to about 70% of the total $R_5$ and $R_6$ moieties are the first component, and from about 30% to about 50% of the total $R_5$ and $R_6$ moieties are the second component.

In one embodiment, from about 10% to about 50% of the total $R_5$ and $R_6$ moieties may be the third component. In another embodiment, from about 10% to about 70% of the total $R_5$ and $R_6$ moieties may be the fourth component.

Hydrophilic, or "soft", components which may be attached to the polyphosphazene polymer backbone include those hereinabove described, as well as methoxy polyethylene glycol, and amino-polyethylene glycol-monomethyl ether.

Hydrophobic, or "hard" components which may be attached to the polyphosphazene backbone include those hereinabove described, as well as phenylalanine ethyl ester, 2-amino-3-phenyl-δ-butyrolactone, and phenylalanine dimethyl glycolamide ester.

Substituents which induce degradation of the polymer, and which may be attached to the polyphosphazene polymer backbone include, but are not limited to, imidazole, 2-amino-δ-butyrolactone, and glycine dimethylglycolamide ester.

Other substituents which also may be attached to the polyphosphazene polymer backbone include inert substituents, such as, but not limited to, glycine ethyl ester, glycine dimethylamide ester, glycine methyl ester, amino-methoxy-ethoxy-ethane. The attachment of such inert compounds aids in enabling one to replace all available chlorines in the polydichlorophosphazene polymer backbone.

As representative examples of polymers which include polyphosphazenes to which are attached hydrophilic ("soft") components, hydrophobic ("hard") components, and possibly degradation inducers, and inert substituents, there may be mentioned the following (percentage values are indicative of the degree of substitution of the substituent in relation to the total degree of substitution):

1. 70% methoxy polyethylene glycol and 30% phenylalanine ethyl ester.
2. 70% amino-polyethylene glycol monomethyl ether and 30% phenylalanine dimethyl glycolamide ester.
3. 60% amino-polyethylene glycol monomethyl ether and 40% 2-amino-δ-butyrolactone.
4. 40% 2-amino-3-phenyl-δ-butyrolactone, 20% imidazole, and 40% amino-polyethylene glycol monomethyl ether.
5. 40% phenylalanine dimethyl glycolamide ester, 30% amino-polyethylene glycol monomethyl ether, and 30% glycine dimethylglycolamide ester.
6. 50% 2-amino-3-phenyl-δ-butyrolactone, 20% imidazole, 20% amino-polyethylene glycol monomethyl ether, and 10% glycine ethyl ester.

The devices of the present invention may be employed as barriers between tissues or barriers between tissue and bone to prevent binding of tissue to tissue or of tissue to bone. Examples of uses of the devices of the present invention include, but are not limited to, barriers between the internal female reproductive organs (eg., uterus, Fallopian tubes, ovaries); barriers between the internal female reproductive organs and the peritoneum; barriers for used during laparoscopy; barriers between peridontal tissue; barriers between cartilages or between cartilage and bone; barriers between digestive organs; spinal barriers; barriers between digestive organs and peritoneum; barriers between the epicardium and surrounding structures such as the pericardium, mediastinal fat, pleura, and sternum; barriers between tendons and tendon sheaths, such as those in the wrist and ankle; bone fracture wraps; barriers between muscle tissue and bone; barriers between the esophagus and mediasternum; barriers between the gall bladder or pancreas and the peritoneum; and barriers for scrotal surgery.

When the device is employed as a barrier between the peritoneum and other internal organs (eg., digestive organs, uterus, etc.), the initial adhesion of the porous second layer to the peritoneum can be improved by the presence of sufficient amount of smaller pores (having a diameter of from about $30\mu$ to $90\mu$). For achieving an improved permanent adhesion by means of connective tissue ingrowth the porous layer should contain a sufficient amount of larger pores (having a diameter of from about $90\mu$ to about $150\mu$).

The devices of the present invention may also be used for guided tissue regeneration. For example, the devices may be used to cover internal perforations, such as, for example, perforations in blood vessels, internal organs, the nasal septum, and the eardrum membrane, and may be used to reconstruct the abdominal wall, or to reinforce areas prone to, or showing scar formation, such as, for example, inguinal herenias. The device therefore acts as a patch for covering the perforation until complete healing, followed by copolymer absorption, is achieved. It is also contemplated that the devices may be employed as a cover for burns, whereby the device acts as a patch until the burn is healed.

The devices of the present invention may be employed as a scaffolding to treat ulcers. The porous layer stimulates the proliferation of fibrous tissue, as a consequence of which, for example, in the case of ulcers, the wound bed becomes more optimal for the regeneration of skin.

The devices of the present invention may also be employed in redirect healing, whereby the devices are employed to protect nerves and organ coverings, and mucosa during the healing process, whereby the formation of fibrous tissue over such nerves, organs, and mucosa is prevented.

The devices may also be employed to prevent the formation of internal blood clots after surgery or traumatic injury.

The devices may also be employed in covering denuded epithelial surfaces or weakened areas such as damaged middle ear mucosa or other mucosal surfaces, thinned vascular walls, or surgically denuded areas, such as, for example, surgically denuded areas of the pelvis.

The devices may also be employed as anti-fibroblastic growth barriers, or as nerve coaptation wraps for connecting or repairing severed nerve ends or for repairing inflamed nerves.

It is also contemplated that in one embodiment, the first layer and/or the second layer of the device may be comprised of a blend of any combination of the polymers hereinabove described, or a blend of any of the polymers hereinabove described and a plasticizer. The plasticizer, when present, may be present in an amount of up to about 50 wt. % of the first layer and/or the second layer, thereby providing increased pliability or elasticity to the first and/or second layer, if desired.

In one alternative, the second layer may be coated with an adhesive such as, but not limited to, cellulose (such as carboxymethyl cellulose, or CMC, and hydroxypropyl methyl cellulose, or HPMC); mucoadhesives, such as, but not limited to, mucin, mucopolysaccharides, polycarbophil, tragacanth, sodium alginate, gelatin, pectin, acacia, and providone; acrylates (such as polyacrylic acid and methyl methacrylate); polyoxyethylene glycol having a molecular weight of from about 100,000 to about 4,000,000; mixtures of zinc oxide and eugenol; a fibrin-glue layer; a chitosan layer; and glucosamine. Such a coating improves initial adhesion of the second layer of the device to tissue, such as the peritoneum.

Alternatively, the adhesive may be admixed with the polymer in the second layer of the device, as the second layer is being formed. In such a manner, a portion of the adhesive will be exposed on the desired surface of the second layer upon formation of the second layer.

The device may also contain pharmaceutical agents (eg., proteins, nucleic acids, antibiotics, etc.) which are placed in the device with an acceptable pharmaceutical carrier. Such agents may diffuse out of the device and into the body after implantation, and/or may be released internally upon degradation of the device, thereby providing a desired therapeutic effect.

Alternatively, the second, or porous, layer of the device may be replaced with a layer which adheres to tissue or bone such that the device effectively prevents the binding of tissue to tissue or tissue to bone. Thus, in accordance with another aspect of the present invention, there is provided a device for preventing the binding of tissue to tissue or of tissue to bone. The device comprises a first layer and second layer. The first layer is selected from the group consisting of a non-porous layer and a porous layer in which essentially all of the pores have a pore size no greater than $3\mu$. The second layer is an adherence layer which comprises at least one material which adheres to tissue and/or bone.

The first, or dense, layer may be formed from the materials hereinabove described, and is believed to act as a barrier layer. The first layer prevents adhesion of tissue to tissue or of tissue to bone, and also prevents the ingrowth of tissue into the first, or dense, layer. The second, or adherence layer, adheres to tissue or bone, and enables the device to become anchored to the tissue without requiring suturing of the device to the tissue.

The second, or adherence layer, may be formed from one or more adhesives such as, but not limited to, cellulose (such as carboxymethyl cellulose, or CMC and hydroxypropyl methyl cellulose, or HPMC), mucoadhesives, such as, but not limited to, mucin, mucopolysaccharides, polycarbophil, tragacanth, sodium alginate, gelatin, pectin, acacia and providone; mixtures of zinc oxide and eugenol; acrylates (such as polyacrylic acid and methyl methacrylate); polyoxyethylene glycol having a molecular weight of from about 100,000 to about 4,000,000; fibrin; chitosan; and glucosamine.

Alternatively, the adherence layer may include materials other than adhesives, such as, for example, polyvinylpyrrolidone, polyethylene glycol, and polycaprolactone.

Such devices may be employed for the same purposes as hereinabove described with respect to the devices which include the porous and dense layers.

In another alternative, the device may be formed from the porous and dense layers as hereinabove described, and then the surface of the porous layer is subjected to a plasma treatment in order to provide a more polar surface of the porous layer. In yet another alternative, only the dense layer is formed, and one of the surfaces of the dense layer is subjected to a plasma treatment to provide a more polar surface of the dense layer.

In each of the above alternatives, the plasma treatment is effected by contacting the porous layer or dense layer with a gas, such as oxygen, for example. When oxygen is employed, oxygen radicals will react with the surface of the porous layer or the dense layer in order to make the surface of the porous layer or dense layer more polar. The plasma treatment thus forms a thin surface layer having a thickness of about $1\mu$ upon the porous layer or the dense layer, which, by virtue of its polarity, becomes more hydrophilic, or wettable, and thereby is able to adhere to tissue or bone.

Such plasma treatment may be effected by placing the device between two metal plates which are connected to an electrical circuit. The circuit's direct current power source periodically sends high voltage pulses to one plate, but the charge on the plate is kept low enough that sparkover does not occur between the plates. Instead, a smaller amount of energy is transferred between the discharge, appears as a purple glow.

The corona discharge does not affect the bulk properties of the device. Instead, it adds energy to the air surrounding the device to change its surface properties. The energy causes many chemical reactions to occur within the air, and the gas surrounding the device becomes a plasma; i.e., the air becomes a mixture of various charged and neutral particles. The plasma in turn makes the surface of the dense layer or porous layer of the device become more polar.

The invention will now be described with respect to the following examples; however, the scope of the present invention is not intended to be limited thereby.

EXAMPLE 1

Films 1 through 10, having porous and/or non-porous layers, and formed from a 55 wt. % polyethylene glycol terephthalate (PEGT)/45 wt. % polybutylene terephthalate (PBT) material, in which the PEGT unit has a molecular weight of 1,000, were formed.

All non-porous or dense films or layers were prepared by liquefying the copolymer in chloroform at a weight ratio of copolymer to chloroform of 1 to 10. The solution is then cast on a glass plate using a film casting apparatus fixed at the desired height.

All porous films or layers were formed by a standard salt-casting technique hereinabove described, wherein the salt particles had sizes described hereinbelow.

Films 2, 4, 5, 6, 7, 8, and 9, which include porous and non-porous layers, were formed by casting a film containing salt particles (i.e., the porous layer) on a glass plate. Chloroform is then evaporated, and the dense (non-porous) layer is applied on top of the porous layer using a casting apparatus. The layers are then formed into a single film which is a composite of the dense layer and the porous layer. The films are then rinsed in distilled water to dissolve the salt particles, dried, cut, packed, and sterilized. Films 7, 8, and 9 are coated with carboxymethylcellulose (CMC). The CMC coating is applied on top of the porous layer before the porous layer is rinsed in distilled water (e.g., 0.5 to 30 wt. % of CMC in distilled water is used to coat the films; films 7, 8 and 9 contain 10 wt. % of CMC per weight of the porous layer). After the addition of CMC, these films are rinsed, cut, dried, packed, and sterilized. Films 1 through 10 had the following characteristics:

Film 1—non-porous monolayer, thickness 20–80$\mu$

Film 2—porous/non-porous bilayer, thickness 250$\mu$, pore diameter of porous layer 150$\mu$–212$\mu$.

Film 3—monolayer formed from a dense layer which was then perforated to form pores having a diameter of 350$\mu$; thickness 70$\mu$;

Film 4—porous/non-porous bilayer; thickness 200$\mu$; pore diameter of porous layer 106$\mu$–150$\mu$;

Film 5—porous/non-porous bilayer; thickness 100$\mu$; pore diameter of porous layer <38$\mu$;

Film 6—porous/non-porous bilayer; thickness 200$\mu$; pore diameter of porous layer 38$\mu$–150$\mu$;

Film 7—porous/non-porous bilayer; thickness 100$\mu$; pore diameter of porous layer <38$\mu$; porous layer coated with carboxymethyl cellulose (CMC);

Film 8—porous/non-porous bilayer; thickness 210$\mu$; pore diameter of porous layer 106$\mu$–150$\mu$; porous layer coated with CMC;

Film 9—porous/non-porous bilayer; thickness 200$\mu$; pore diameter of porous layer 38$\mu$–150$\mu$; porous layer coated with CMC;

Film 10—porous monolayer; thickness 180$\mu$; pore diameter 38$\mu$–150$\mu$.

Each of Films 1 through 10 was wetted and then attached to a glass plate.

It was found that Films 1 and 3 did not attach to the glass plate, Film 2 showed some attachment, while Films 4 through 10 showed good attachment. Films 7 through 9 showed the best attachment.

Films 4, 6, 8, and 9 were also made having the following soft-to-hard component proportions:

70 wt. % PEGT/30 wt. % PBT;
40 wt. % PEGT/60 wt. % PBT; and
55 wt. % PEGT/45 wt. % PBT
for the porous layer, and in proportions of:
70 wt. % PEGT/30 wt. % PBT;
60 wt. % PEGT/40 wt. % PBT;
55 wt. % PEGT/45 wt. % PBT; and
50 wt. % PEGT/50 wt. % PBT
for the non-porous layer, and having a PEGT unit of a molecular weight of 600 or 1,500. These films also showed attachment to glass.

EXAMPLE 2

Films 1, 2, and 3 were prepared as in Example 1. After rinsing the films were air dried, precut, vacuum sealed, and sterilized with gamma radiation (25/kGy). In this example, Film 1 has a thickness of 42$\mu$.

A standard model was then developed to evaluate the films as barriers to prevent post-operative adhesions. In the standard model, 10 female Wistar rats, each weighting from 180 to 200 grams, were used. The standard model consisted of excision of a defect in the pelvic sidewall which was sutured with three vicryl 5–0 sutures. The uterine horn was then traumatized by clamping and sutured cranially and/or distally to the pelvic sidewall. No attempt at hemostasis was made.

Films 1, 2, and 3, as well as control films of Interceed® (Johnson & Johnson Med., Amersfoort, Netherlands), were placed between the pelvic sidewall defect and the uterine horn without suturing. When Film 2 was placed, the porous layer faced the peritoneum. The experiment also included a control group of sham-operated rats, operated according to the standard model procedure but without interposition of a film. Barriers of Films 1, 2, or 3, or the control Interceed® film, or sham operations were carried out in a total of 23 rats.

Each rat had two implantation sites. The total numbers of each type of implant were as follows:

| | |
|---|---|
| Film 1 - | 11 |
| Film 2 - | 12 |
| Film 3 - | 13 |
| Interceed ® - | 4 |
| Sham (no implant) - | 6 |
| TOTAL - | 46 |

After two weeks the adhesions were macroscopically scored, dissected and fixed by immersion in 1.5% glutaraldehyde in 0.1M cacodylate buffer (pH=7.4). After dehydration they were embedded in glycol methacrylate (GMA) or paraffin for light microscopy. Part of the material was processed for scanning electron microscopy (sem).

The percentage of the defect that was covered by adhesions was scored. The area to be scored was divided into eight areas, each area representing 12.5% of the total area. The score ranged from minimally 0 to maximally 8. Percentage error for the adhesions calculated in each group of rats was determined by the least significant difference-multiple range test method.

The results were as follows:

Standard model—In the standard model, the adhesions that were seen macroscopically came from the pelvic fat body, the omentum, or the uterine horn and were attached to the peritoneal defect. An adhesion percentage of 84% (±23) was found.

Film 1—Film 1 detached and adhesion formation on the peritoneal defect was 68.2 (±34.1).

Film 2—In 8 of 12 films, the film remained at its original position. A number of films showed adhesions, mostly on cracks and damaged areas. The total percentage of adhesion formation (either on the defect or on the remaining films), was 43.8% (±39.7). Scanning electron microscopy showed that the films remained in place were completely covered with confluent mesothelium. Light microscopy showed ingrowth of vascularized fibrous tissue into the porous layer, and a single continuous layer of flattened mesothelium with a morphology resembling that of normal mesothelium.

Film 3—The perforated films all remained in place and an adhesion percentage of 69.2% (±34.1) was found.

Interceed®—An adhesion percentage of 75% (±33.9) was found with the Interceed® films.

Sham—The sham-operated animals had an adhesion percentage of 79.2% (±23.3).

The above results indicate that a film having a porous layer and a dense layer of a polyethylene oxide/polybutylene terephthalate copolymer is the most effective in reducing the formation of post operative adhesions in the rat.

EXAMPLE 3

Film 4 (from Example 1) formed from a copolymer of 55 wt. % polyethylene glycol terephthalate/45wt. % polybutylene terephthalate, is compared with Interceed® and sham-operated animals for preventing post-operative adhesions. The operation technique and evaluation methods are those of Example 2. Operations were performed on 15 rats, wherein two implantation sites were formed in each rat, for a total of 30 sites. Ten sites received Film 4, ten sites received Interceed®, and ten sites were sham sites (no implants). The results are shown in Table I below.

TABLE 1

| | adhesion score/% of adhesion | | |
|---|---|---|---|
| Sample | Film 4 | Interceed ® | Sham |
| 1 | 4/50% | 8/100% | 7/87.5% |
| 2 | 8/100%# | 7/87.5% | 5/62.5% |
| 3 | 7/87.5%# | 6/75% | 6/75% |
| 4 | 2/25% | 6/75% | 5/62.5% |
| 5 | 5/62.5%# | 0/0% | 5/62.5% |
| 6 | 0/0% | 8/100% | 8/100% |
| 7 | 0/0% | 8/100% | 8/100% |
| 8 | 0/0% | 8/100% | 7/87.5% |
| 9 | 8/100%# | 7/87.5% | 6/75% |
| 10 | 8/100%# | 8/100% | 8/100% |
| Total | 42/52.5% | 66/82.5% | 65/81.25% |

\# - film detached.

The above results show that Film 4 had an overall adhesion percentage of 52.5% (±43.7), as compared with 82.5% (±30.7%) with Interceed®, and 81.25% (±15.9) with the sham-operated rats. Also, with the Film 4 barriers which did not detach, the adhesion percentage was about 18%.

Film 4 also had a hemostatic effect in that immediately after implantation, Film 4 absorbs blood.

The above results indicate that the adhesion percentage of the implants of Film 4 differ significantly from those of Interceed and from the sham-operated group.

Routine scanning electron microscopy and light microscopy carried out with barriers made of Film 4 showed that the mesothelium (epihelium covering the peritoneum) had overgrown the Film 4 barrier and ingrowth took place into the pores of the porous layer of the Film 4 barrier. It is concluded that the mesothelium regenerates over the Film 4 barrier (contrary to the Interceed® barrier) so that the original epithelium was restored. On account of this result the restored epithelium surfaces of both the mesothelium and the uterine horn prevent the adhesion between both tissues in a natural way. After some time the Film 4 barrier disappears by biological degeneration (resorption) underneath the mesothelial layer.

EXAMPLE 4

Surgery was performed on eight adult (age 2–3 years) mongrel male dogs, in four groups of two as follows:

Using standard aseptic techniques, laminectomy surgery was performed on each dog under halothane gas anesthesia, and each dog was monitored by electrocardiogram and heart monitors. A midline dorsal skin incision was made from the $T_{12}$ vertebra to the sacrum. The longitudinal paraspinous muscles were subperiosteally stripped and retracted from the posterior elements, and the posterior arch of the vertebral bodies of each of the $T_{13}$-$L_1$, $L_2$-$L_3$, $L_4$-$L_5$, and $L_6$-$L_7$ levels were exposed. Four non-contiguous implant sites were created, each site being separated by one intact lamina. Excision of bony elements then was carried out with a high speed pneumatic burr, which created a 1.5 cm×1.0 cm defect. Soft tissues, including the ligamentum flavium, then were lifted carefully from the dura. The dura was manipulated gently in the course of removing the epidural fat at the level of the defect but was not intentionally abraded. Each animal then was implanted with a bilayer 100 mm×100 mm sheet of a polyethylene glycol terephthalate/polybutylene terephthalate (PEGT/PBT) segmented copolymer, having a wt-% ratio of PEGT to PBT of 60/40 at two implant sites. The sheet has a dense layer and a porous layer having a pore size of from 75 to 212 microns. The sheets were shaped with scissors during surgery to accommodate the defect site. One animal in each group had the porous layer of the sheet placed directly on the dura, while the other animal had the dense layer of the sheet placed directly on the dura. Each animal also received at one implant site an implant of an autogenous free fat graft obtained from superficial layers of the surgical site, and one implant site of each animal received no implant.

The animals were administered intramuscular antibiotics for five days after surgery. Intramuscular injections of methylprednisolone sodium succinate were administered for 48 hours after surgery to reduce inflammation adjacent the spinal cord. Intramuscular injections of butorphanol were administered post-operatively for pain control as necessary.

One group of dogs was sacrificed two weeks after surgery; one group of dogs was sacrificed four weeks after surgery; one group of dogs was sacrificed eight weeks after surgery; and one group of dogs was sacrificed twelve weeks after surgery. Sacrifice was effected by administering to each animal an overdose of a barbiturate solution (Beuthanasia-D). A gross pathologic examination of all implant sites was performed. The operative section of the spine was examined en bloc, and then stored in saline soaked diapers. Anterior-posterior and lateral radiographs of the specimens were obtained and evaluated.

Following radiographic studies, all spines were stripped of soft tissue to expose the implant sites. All tissues above the defect sites were grossly dissected. The dissections were photographed with the aid of a photographic stereomicroscope. The gross dissections were carried down to the dura, without destruction of local histology if possible, for visual inspection of adhesion presence. The defect sites then were evaluated for scar formation. Scar formation was graded as follows: 0=no scarring; 1=mild scarring; 2—moderate scarring; and 3=extensive scar formation. The scar formation for each implant site for each dog sacrificed at 2 weeks, 4 weeks, and 8 weeks is given in Table I below. Grading could not be performed for the dogs sacrificed at 12 weeks.

TABLE I

| Sacrifice (Weeks post-surgery) | Gross Dissection Grading Results | | |
|---|---|---|---|
| | Dog No. | PEGT/PBT | Implant Site Fat Graft | Control |
| 2 | 1 | 0 | 1 | 2 |
| 2 | 2 | 0 | 1 | 2 |
| 4 | 1 | 0 | 1 | 2 |
| 4 | 2 | 0 | 2 | 3 |
| 8 | 1 | 0 | 3 | 3 |
| 8 | 2 | 1 | 2 | 3 |

Following gross dissection, each implant site was isolated and fixed by immersion in 10% formalin solution. Following fixation, the specimens were decalcified and dehydrated in graduated ethyl alcohol solutions form 70% to 100%. The specimens then were embedded in paraffin and sectioned on a microtome into sections approximately 5 microns thick. Three levels were obtained of each implant site so as to view sections throughout the entire implant site. All sections were stained with either Hemetoxylin and Eosin (H&E), Mason's Tri-Chrome, or Giemsa. The sections were graded for scar formation by using the 0–3 scale hereinabove described with respect to the gross dissection. The results for each dog are given in Table II below.

TABLE II

| Sacrifice (Weeks post-surgery) | Histologic Grading Results | | |
|---|---|---|---|
| | Dog No. | PEGT/PBT | Implant Site Fat Graft | Control |
| 2 | 1 | 0 | 0 | 2 |
| 2 | 2 | 0 | 1 | 2 |
| 4 | 1 | 0 | 3 | 2 |
| 4 | 2 | 0 | 1 | 3 |
| 8 | 1 | 0 | 1 | 3 |
| 8 | 2 | 1 | 0 | 3 |
| 12 | 1 | 1 | 0 | 3 |
| 12 | 2 | 1 | 1 | 3 |

The above gross dissection and histologic grading results indicate that the barrier material of the present invention provides improved resistance to adhesions and scar formation following spinal surgery as compared with fat graft implants and sites which received no implants.

It is to be understood, however, that the scope of the present invention is not to be limited to the specific embodiments described above. The invention may be practiced other than as particularly described and still be within the scope of the accompanying claims.

What is claimed is:

1. A device for preventing the binding of tissue to tissue or of tissue to bone, comprising a composite of a first layer and a second layer, wherein each of said first layer and said second layer comprises a biodegradable segmented copolymer which comprises a first component which is a polyalkylene glycol; and a second component which is a polyester formed from an alkylene glycol having from 2 to 8 carbon atoms and a dicarboxylic acid, wherein said first layer is selected from the group consisting of a non-porous layer and a porous layer in which essentially all of the pores have a pore size no greater than $3\mu$, and wherein said second layer includes pores having a pore size or at least about $30\mu$.

2. The device of claim 1 wherein said polyalkylene glycol is selected from the group consisting of polyethylene glycol, polypropylene glycol, and polybutylene glycol.

3. The device of claim 1 wherein said polyalkylene glycol is polyethylene glycol.

4. The device of claim 1 wherein said polyester is selected from the group consisting of polyethylene terephthalate, polypropylene terephthalate, and polybutylene terephthalate.

5. The device of claim 4 wherein said polyester is polybutylene terephthalate.

6. The device of claim 1 wherein said biodegradable segmented copolymer is a polyethylene glycol/polybutylene terephthalate copolymer.

7. The device of claim 1 wherein said ester has the following structural formula:

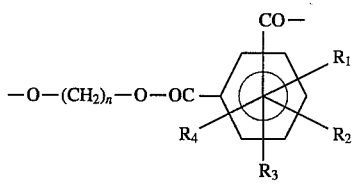

wherein n is from 2 to 8, and each of $R_1$, $R_2$, $R_3$ and $R_4$ is hydrogen, chlorine, nitro-, or alkoxy, and each of $R_1$, $R_2$, $R_3$, and $R_4$, is the same or different.

8. The device of claim 1 wherein mid second layer includes pores having a pore size of from about 30μ to about 250μ.

9. The device of claim 1 wherein said polyalkylene glycol is present in said copolymer in an amount of from about 30 wt. % to about 80 wt. %.

10. The device of claim 9 wherein said polyalkylene glycol is present in said copolymer in an amount of from about 50 wt. % to about 80 wt. %.

11. The device of claim 1 wherein said polyester is present in said copolymer in an amount of from about 20 wt. % to about 70 wt. %.

12. The device of claim 11 wherein said polyester is present in said copolymer in an amount of from about 20 wt. % to about 50 wt. %.

13. A device for preventing the binding of tissue to tissue or of tissue to bone, comprising a composite of a first layer and a second layer, wherein each of said first layer and said second layer comprises a biodegradable copolymer, said copolymer being a segmented thermoplastic copolymer comprising a plurality of recurring units of a first component and of a second component, wherein said first component comprises from about 30 wt. % to about 80 wt. %, based on the weight of said copolymer, of units having the formula:

—OLO—CO—R—CO—, wherein L is selected from the group consisting of a divalent radical remaining after removal of terminal hydroxyl groups from a poly (oxyalkylene) glycol; and a polymer including a first moiety and a second moiety, said first moiety being a polyalkylene glycol and said second moiety being selected from the group consisting or glycine anhydride; alloxan; uracil; 5,6-dihydrouracil; glycolic acid; lactic acid; and lactones; and said second component comprises from about 20 wt. % to about 70 wt. %, based upon the weight of said copolymer, of units having the formula:

—OEO—CO—R—CO—, wherein E is an organic radical selected from the group consisting of a substituted or unsubstituted alkylene radical having from 2 to 8 carbon atoms, and R is a divalent radical remaining after removal of carboxyl groups from a dicarboxylic acid, wherein said first layer is selected from the group consisting of a non-porous layer and a porous layer in which essentially all the pores have a pore size no greater than 3μ, and said second layer includes pores having a pore size of at least about 30μ.

14. The device of claim 13 wherein said poly (oxyalkylene) glycol is selected from the group consisting of poly (oxethylene) glycol, poly (oxypropylene) glycol, and poly (oxybutylene) glycol.

15. The device of claim 14 wherein said poly (oxyalkylene) glycol is poly (oxyethylene) glycol.

16. The device of claim 13 wherein E is an alkylene radical having from 2 to 4 carbon atoms.

17. The device of claim 16 wherein said second component is selected from the group consisting of polyethylene terephthalate, polypropylene terephthalate, and polybutylene terephthalate.

18. The device of claim 17 wherein said second component is polybutylene terephthalate.

19. The device of claim 13 wherein said poly (oxyalkylene) glycol is poly (oxyethylene) glycol, and said second component is polybutylene terephthalate.

20. The device of claim 13 wherein said first component is present in the copolymer in an amount of from about 50 wt. % to about 80 wt. %.

21. The device of claim 13 wherein said second component is present in the copolymer in an amount of from about 20 wt. % to about 50 wt. %.

22. The device of claim 13 wherein said second layer includes pores having a pore size of from about 30μ to about 250μ.

* * * * *